United States Patent [19]

Coffman

[11] Patent Number: 5,325,415
[45] Date of Patent: Jun. 28, 1994

[54] APPARATUS FOR CONDUCTING CRANIAL X-RAY TOMOGRAPHY AND RADIOGRAPHY

[76] Inventor: George W. Coffman, 12307 Rip Van Winkle, Houston, Tex. 77024

[21] Appl. No.: 926,814

[22] Filed: Aug. 7, 1992

[51] Int. Cl.$^5$ .............................................. A61B 6/14
[52] U.S. Cl. ...................... 378/38; 378/168; 378/171
[58] Field of Search ................ 378/38, 168, 170, 177, 378/179, 180, 191, 205, 208, 196

[56] References Cited

U.S. PATENT DOCUMENTS

| | | | |
|---|---|---|---|
| 3,743,832 | 7/1973 | Wright | 378/168 |
| 4,145,611 | 3/1979 | Valila | 378/168 |
| 5,148,454 | 9/1992 | Coffman | 378/38 |

*Primary Examiner*—David P. Porta
*Assistant Examiner*—Don Wong
*Attorney, Agent, or Firm*—James L. Jackson

[57] ABSTRACT

Apparatus is provided for cranial X-ray tomography and radiography which includes a housing having a horizontal support projecting forwardly therefrom. A pivot arm is pivotally supported by the horizontal support by means of a pivot bearing. The pivot arm provides support for a narrow beam tomographic X-ray source and film holder and is provided with a guide bearing which has guided relation with a horizontal guide shaft within the housing to provide for horizontal pivotal oscillation of the support arm during tomographic procedures. The pivot arm is controllably moved by means of a reversible electric motor which imparts driving movement to the guide bearing by means of a flexible drive element. The electric motor is controllably energized and deenergized by means of electrical circuitry incorporating limit switches which limit pivotal movement of the pivot arm. A patient head locator is provided in the form of a locator device which projects laterally from the fixed horizontal support and adjustably presents a mouthguard-type dentition engaging element so as to enable patient location with an anatomical area of interest located precisely at the focal point of the X-ray source. Proper location is achieved by means of an elongate pointer which is removably positioned along the axis of rotation of the pivot arm with its lower pointed end precisely at the focal point of the X-ray source.

20 Claims, 3 Drawing Sheets

FIG. 4
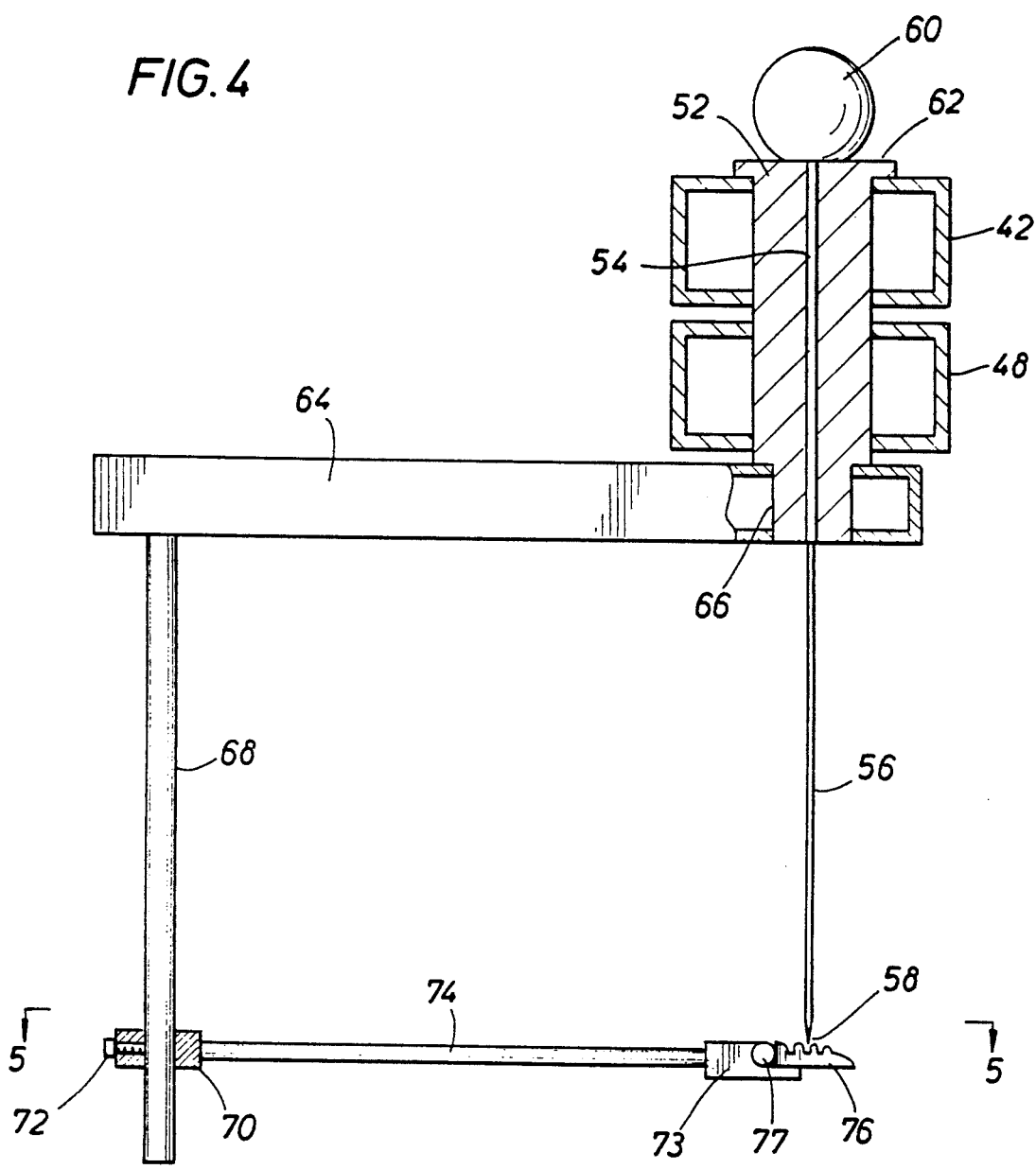
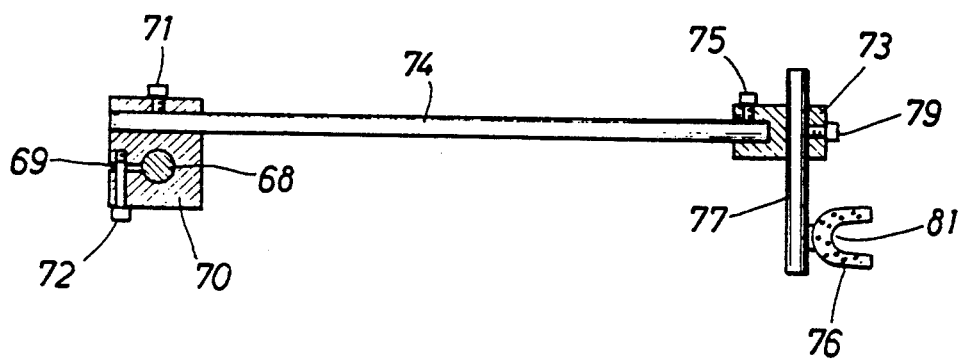
FIG. 5

APPARATUS FOR CONDUCTING CRANIAL X-RAY TOMOGRAPHY AND RADIOGRAPHY

FIELD OF THE INVENTION

This invention relates generally to cranial X-ray tomography and radiography and more specifically is directed to X-ray tomographic apparatus for cranial X-ray tomography and radiography to accomplish successive X-ray exposures and thereby achieve multiple X-ray images representing spaced X-ray cuts of a cranial anatomical site of interest, such as the alveolar arch, for example.

BACKGROUND OF THE INVENTION

X-ray tomographic apparatus has been marketed for many years for the purpose of conducting X-ray cranial tomography to obtain plural, evenly spaced X-ray cuts of cranial sites of interest such as the temporo-mandibular joint for example. In every case tomographic apparatus is positioned such that an X-ray source and an X-ray film cassette are positioned on opposite sides of the patient's anatomical site of interest. The X-ray source and film cassette are movable about the anatomical site of interest while the X-ray source is energized to achieve each tomographic image on the film. Typically the X-ray source and film holder are supported on a movable support that is rotated about a pivot point during film exposure. This pivotal motion blurs out all anatomy in front of and behind the focal point of the X-ray source and thus provides an X-ray exposure that is representative of a cross-section taken through the anatomical area of interest. In many cases, depending upon the character of X-ray tomography that is desired, the apparatus accomplishing rotary movement of the X-ray head and film holder will move either the X-ray head or film holder or both along an elliptical path such as substantially conforming to the configuration of the mandible of the patient. This type of apparatus is widely utilized in dentistry and for maxillo-facial surgery although it has a number of other uses as well. X-ray tomography is especially important in cases where confirmation of precision location is desired for dental implant location in the alveolar arch.

THE PRIOR ART

For the most part, the X-ray tomography apparatus that has been developed and marketed accomplishes rotation of the X-ray head and film support arm about a substantially vertical axis so that the arcuate movement of these components is in a substantially horizontal plane. U.S. Pat. No. 4,675,888 of Gastrin; U.S. Pat No. 4,823,369 of Guenther, et al.; and U.S. Pat. No. 4,852,134 of Kinanen, et al. are representative of simple vertical axis rotation of an arm that supports the X-ray head and film holder. More complex rotary movement of a support for an X-ray head and film holder, including relative lateral movement during rotation is evidenced by U.S. Pat. No. 4,741,007 of Virta, et al.; U.S. Pat. No. 4,756,014 of Doebert; U.S. Pat. No. 4,783,793 of Virta, et al.; U.S. Pat. No. 4,811,372 of Doebert, et al.; U.S. Pat. No. 4,813,060 of Heubeck, et al.; U.S. Pat. No. 4,856,038 of Guenther, et al.; U.S. Pat. No. 4,907,251 of Mork, et al.; and U.S. Pat. No. 4,985,907 of Moteni. Although each of the U.S. Patents previously identified describe rotation of a support for an X-ray head and film holder about a vertical axis, one patent, namely U.S. Pat. No. 4,974,243 of McArdle, et al. discloses a positioning system for x-ray tomography including an X-ray head and film support arm or spar that rotates about a fixed horizontally oriented axis. With respect to the '243 patent of McArdle, et al., it should be noted that the head fixator mechanism 50 includes an associated X, Y and Z positioning mechanism 52, thus, the head fixator or cephalostat is positionable utilizing X, Y and Z translational mechanisms representing adjustment in each of X, Y and Z cartesian coordinates. Reference is also made to U.S. Patent application Ser. No. 07/750,510 now U.S. Pat. No. 5,148454 of George W. Coffman, of common inventorship herewith, filed on August 27, 1991, and entitled APPARATUS FOR CONDUCTING CRANIAL X-RAY TOMOGRAPHY AND RADIOGRAPHY.

Although X-ray tomography systems such as that shown by the '243 patent of McArdle, et al. are quite functional, nevertheless, they are for the most part of quite complicated design and function and therefore are quite expensive from the standpoint of purchase, installation and repair. It is desirable to provide X-ray tomography apparatus having characteristics of low cost, simplicity and yet being efficient from the standpoint of functionality.

SUMMARY OF THE INVENTION

It is a primary feature of the present invention to provide novel apparatus for cranial X-ray tomography and the like through use of an X-ray tomography system that permits the cranial anatomy of a human subject to remain fixed during multiple spaced tomographic X-ray exposures.

It is another feature of the present invention to provide novel X-ray tomographic apparatus incorporating a support for an X-ray head and film holder that is horizontally pivotal about a vertical axis and wherein the vertical axis is coincident with the focal point of the X-ray source.

Even further, it is a feature of this invention to provide a simple mechanical mechanism for controlling horizontal pivotal movement of the source and film cassette holder about a vertically oriented axis to enable efficient, accurate use of the apparatus for achieving accurately located X-ray cuts of a cranial anatomical site of interest.

It is also a feature of this invention to provide novel apparatus for X-ray tomography and radiography which establishes precise patient head fixation by means of patient dentition engagement with a fixed locator.

It is also a feature of this invention to provide novel apparatus for X-ray tomography and radiography which incorporates a removable locating pointer which is positionable in coincident relation with the focal point of the X-ray source to thus enable precision location of the patient head locator relative to said focal point.

Other and further features of the present invention which will become apparent upon a complete understanding of the present invention, are considered to be within the spirit and scope of this invention.

Briefly, X-ray tomographic apparatus constructed in accordance with the present invention includes a housing structure such as might be supported by the wall of a dental operatory or the like. Alternatively, the housing structure may be floor supported if desired. From the housing, there is forwardly projected a generally horizontal support structure. A patient head fixator assembly is fixedly supported by the horizontal support structure and incorporates an adjustable head positioner that is adapted for positioning engagement by the dentition of the patient. The adjustable head positioner is specifically designed for locating the head and in particular the maxilla and mandible of the patient's cranial anatomy at a fixed location, with an anatomical site of interest, such as the alveolar arch of the maxilla or mandible, located at the focal point of the X-ray source.

A removable pointer is extended through a vertical passage in a pivot controlling element of the horizontal support structure and is of such length that its lower, pointed end is positioned precisely at the focal point of the X-ray source. A template which is formed to the dentition of the patient is supported for adjustable positioning by the adjustable head positioner of the horizontal support structure and is positionable in relation to the focal point of the X-ray source such that when engaged by the dentition of the patient, the anatomical site of interest will be precisely positioned at the focal point to enable the development of a sharp cross-sectional X-ray image of the site. The pointer is removed to permit engagement of the locator template by the dentition of the patient. The patient locator template is typically in the general form of a mouthguard-shaped device which is adjustably supported by a support rod depending from a lateral support arm of the horizontal support. Prior to its use, the material of the patient locator template device is formed to the dentition of the patient, typically by having the patient bite on the device prior to curing and setting of a deformable polymer material which is supported by a substrate structure.

At the forward portion of the horizontal support is pivotally mounted a movable pivot arm which is controllably pivoted during imaging and return cycles by means of a reversible electric motor. The motor drives an elongate belt or cable which imparts linear movement to a bearing along a horizontally mounted guide shaft. The bearing is pivotally connected to the movable arm and thus imparts pivotal movement to the arm as it moves linearly along the guide shaft during energization of the electric motor. The pivotal arm is stopped at respective extremities of its travel by means of limit switches in control circuits that deenergize the electric motor when engaged by the pivot arm or by positioning devices projecting from the pivot arm. At the inner extremity of the pivot arm is fixed an X-ray source which generates a narrow beam of X-radiation that is suitable for precision X-ray tomography. A timing circuit, being a component part of the electrical motor control circuitry, ensures that the X-ray source is just beginning a pivotal traverse as the X-ray head initiates its firing sequence. At the opposite end of the pivotal arm is mounted a cassette holder enabling releasable positioning of an X-ray film cassette that is movably positionable relative to the holder in the event multiple exposures might be desirable on a single sheet of X-ray film. As the pivot arm moves about its pivot the X-ray source and the cassette holder and X-ray film cassette which are located at or near respective ends of the pivot arm are moved accurately while maintaining a fixed relation with one another.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

IN THE DRAWINGS

Figure 1:
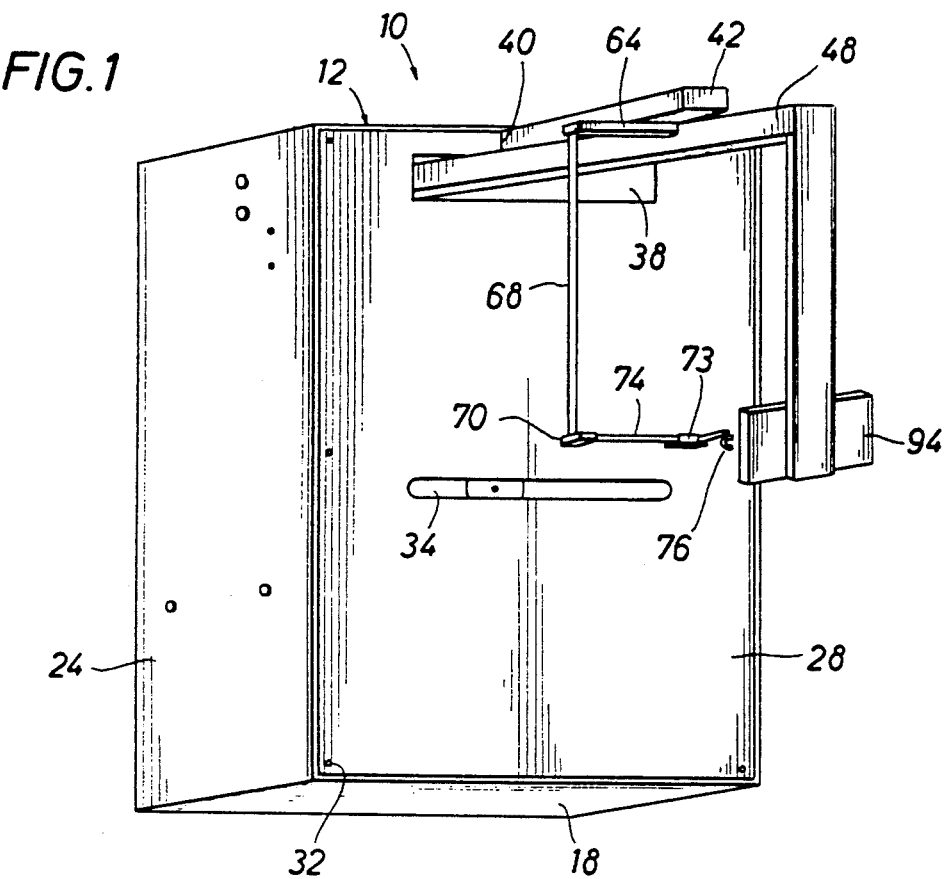

FIG. 1 is an isometric illustration of apparatus for cranial X-ray tomography and radiography which is constructed in accordance with the present invention.

Figure 2:
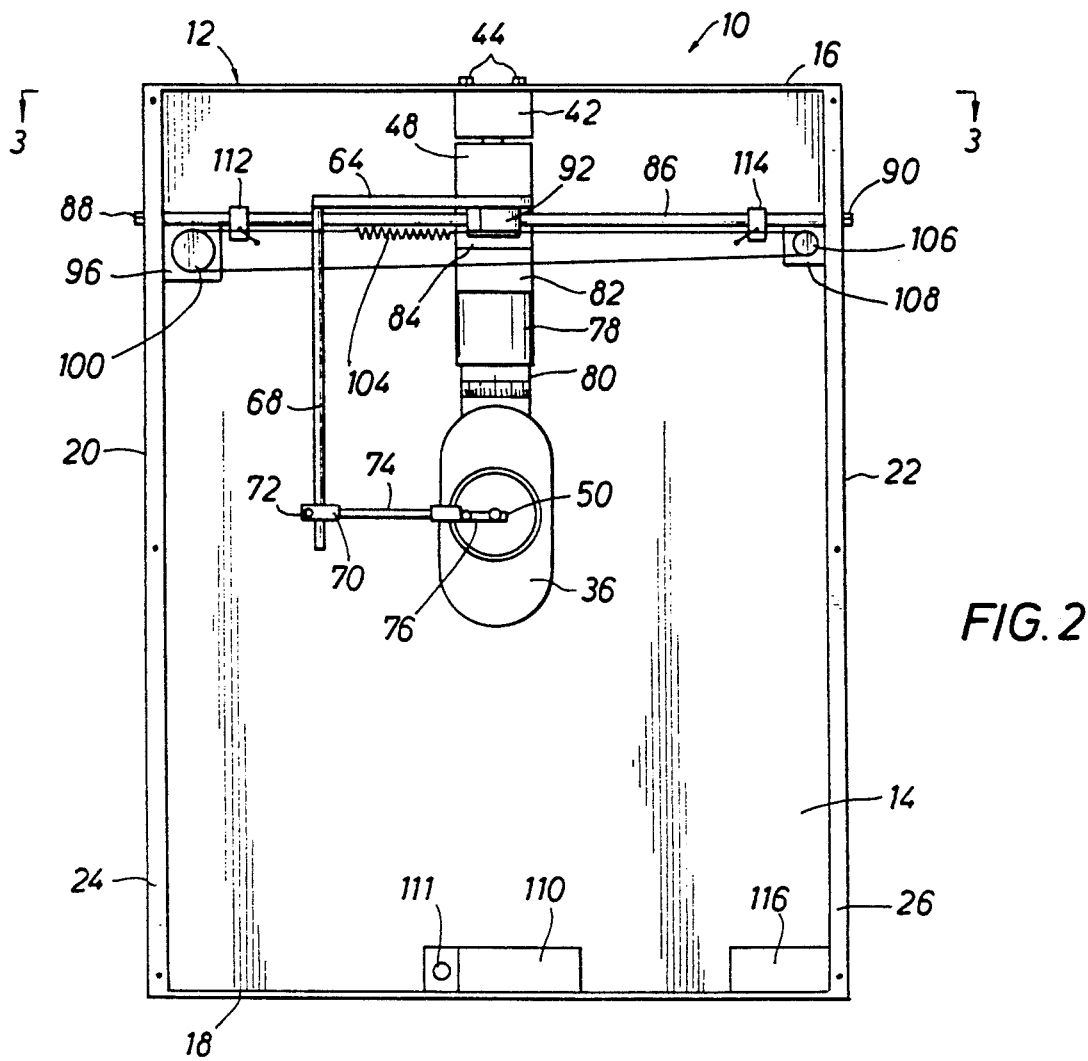

FIG. 2 is a front elevational view of the apparatus of FIG. 1, with the front panel thereof removed to expose the internal mechanism thereof.

Figure 3:
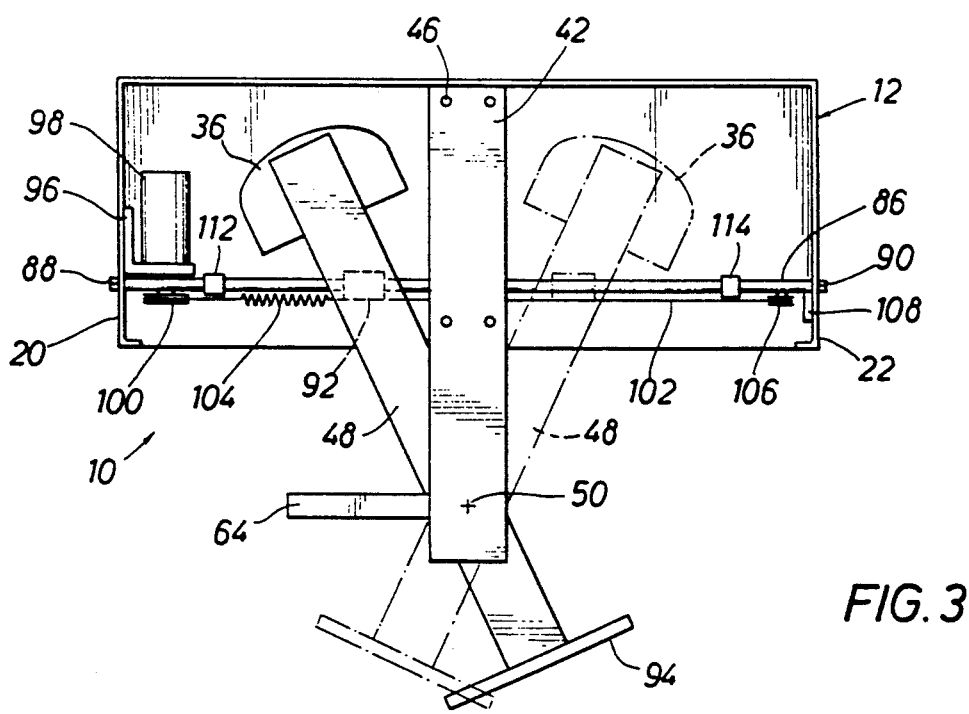

FIG. 3 is a plan view of the preferred embodiment of this invention which is taken along line 3—3 of FIG. 1.

FIG. 4 is a partial sectional view illustrating the head fixator portion of the cranial X-ray tomography and radiography apparatus of FIGS. 1-3.

FIG. 5 is a partial plan view taken along line 5—5 of FIG. 4 and showing further details of the patient head fixator mechanism.

Figure 6:
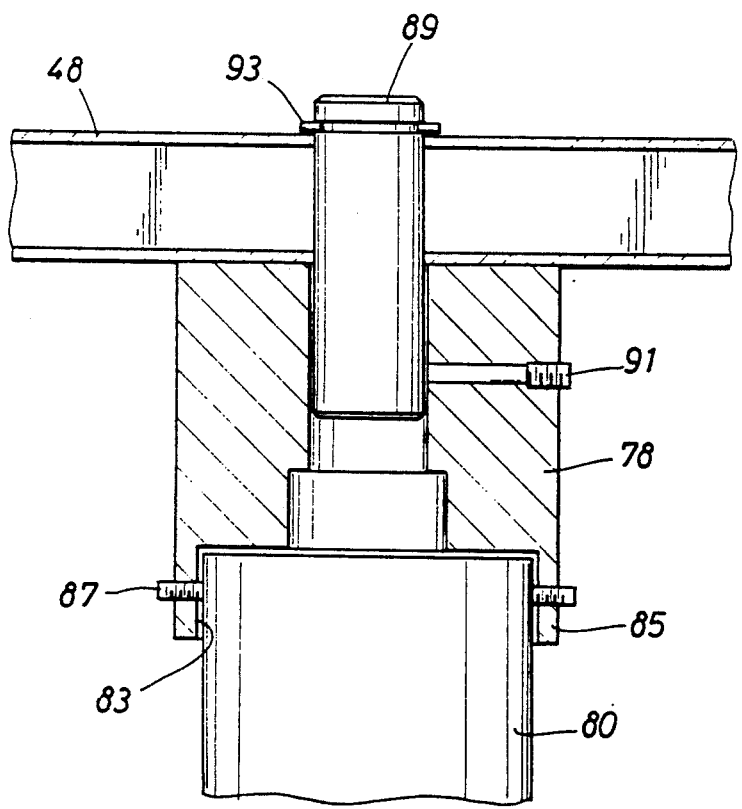

FIG. 6 is a partial sectional view of the pivot arm structure illustrating the support structure for the X-ray source in detail.

DETAILED DESCRIPTION OF PREFERRED EMBODIMENT

Referring now to the drawings and first to FIGS. 1-3, apparatus for conducting cranial X-ray tomography and radiography is shown generally at 10 and includes a housing structure shown generally at 12. The housing 12 incorporates a rear wall panel 14 which is preferably adapted to be secured to the wall structure of a dental or medical operatory but which may be mounted in any suitable manner. Forwardly from the rear wall 14 projects top and bottom walls 16 and 18 and side walls 20 and 22. At their respective forward portions the side walls 20 and 22 are provided with mounting flanges 24 and 26 which provide for support of a removable lower front wall panels 28. The flanges 24 and 26 are provided with screw holes 30, enabling the front wall panel to be connected thereto by means of a plurality of panel support screws 32 as is evident from the isometric illustration of FIG. 1. The top of the front wall panel 28 defines a radiation opening 34 through which a beam of x-radiation is transmitted by means of a suitable X-ray source 36. The top front wall panel 28 further defines a generally rectangular opening 38 through which projects a pivot arm and a generally rectangular upper recess 40 through which projects a horizontal support arm 42. As shown in FIG. 1, the horizontal support arm 42 is of generally rectangular cross-sectional configuration through it may be of any other suitable configuration without departing from the spirit and scope of this invention. The support arm 42 is secured to the top panel 16 of the housing 12 by means of a plurality of bolts 44. The horizontal support arm is thus fixed relative to the housing structure and includes a section extending forwardly of the front wall of the housing as is evident from the isometric illustration of FIG. 1 and the plan view of FIG. 3. The movable support arm 48, which is also referred to herein as a pivot arm, is pivotally supported near the forward, free extremity of the horizontal support 42 and defines an axis of rotation 50 as shown in FIG. 3. The movable or pivotal support arm 48 is secured to the fixed horizontal support 42 by means of a pivot bearing 52 which is shown in FIG. 4 and also shown at the upper portion of FIG. 2. The pivot bearing 52 defines a vertical passage 54, which is coincident with the axis of rotation 50, through which is removably received an elongate pointer shaft 56 having a locator point 58 at the lower extremity thereof which precisely indicates the axis of rotation 50. At its upper end the pointer shaft 56 is provided with a placement handle or knob 60 which is of sufficient dimension to provide a stop for engagement with the upper extremity 62 of the bearing 52 to thereby limit downward movement of the pointer shaft. The pointer shaft is of such length that, in the fully inserted position of the pointer, as shown in FIG. 4, the sharp, locator point 58 thereof is positioned precisely at the focal point of the X-ray source as well as coincident with the axis of rotation 50. A transverse locator arm 64 is fixed to a reduced diameter lower end portion 66 of the bearing 52 such as by means of a set screw or by any other suitable means of fixation. A vertical locator rod 68 of cylindrical cross-sectional configuration is fixed to and depends from one end of the transverse locator arm 64 as shown in FIG. 4. While the transverse locator arm 64 is preferably composed of metal, the vertical locator rod 68 may be composed of a suitable polymer material such as Lucite TM. The locator arm and locator rod may also be composed of any other suitable materials. At the lower end of the locator rod 68 is provided an adjustable support 70 which is adjustably positioned relative to the locator rod 68 by means of a split-clamp 69 which is tightened by a bolt or set screw 72 or the like. From a bore of the support 70 projects a horizontal positioning arm 74 which is releasably secured to the support 70 by a set screw 71. The support arm is in turn releasably secured within a bore of a support block 73 by a set screw 75. A second support arm 77 extends through a bore of the support block 73 by a set screw 75. A second support arm 77 extends through a bore of the support block 73 and is secured by a set screw 79. Toe the support arm is fixed a structural substrate 81 which is generally in the form of a dental impression tray. The structural substrate is filled with a curable polymer impression material and deformed by the patient's dentition to thus define a patient head fixator assembly 76. The patient will bite on the U-shaped head positioning device 76 so as to cause the patient's dentition to engage the mating geometry of the locator device. When this is accomplished. The mandibular and maxillary dentition of the patient and thus the anatomical site of interest will be precisely located with respect to the focal point of the X-ray source.

The X-ray source 36 includes a support connector 78 which provides support for the X-ray head by means of an adjustable support structure 80 having appropriate indicia for adjustment of the horizontal angle of the X-ray beam emanating from the X-ray source. The support is connected to or integral with, a support bracket 82 which is in turn fixed to the lower portion of the movable pivot arm 48. The bracket 82 may be connected directly to the lower portion of the pivot arm 48 or, if desired, the X-ray source bracket 82 may be fixed to a mounting bracket 84 to thus provide for fixed support of the X-ray source assembly relative to the movable pivot arm 48. If desired, the X-ray source may have its adjustable support structure 80 connected directly to the pivot arm 48 in the manner shown in FIG. 6. The adjustable support 80, in this case, is received within a receptacle 83 defined by a cylindrical flange 85 depending from the lower portion of the connector 78 and secured by set screws 87. A support pin 89 secured to the connector by a set screw 91 extends through an aperture or bore in the pivot arm. A retainer clip 93 is then placed within a receptacle in the upper end of the pin 89. Additionally, one or more set screws may be employed to stabilize the retainer pin relative to the pivot arm.

During the telegraphic X-ray procedure, it is appropriate that the X-ray source maintain its focal point at the axis of rotation 50 while the dentition of the patient is also fixed with its area of interest located at the focal point 50. To accomplish this feature, as shown in FIGS. 2 and 3, there is provided within the housing structure 12 an elongate, horizontal guide bar 86 which is fixed to the opposed side walls 20 and 22 by means of bolts 88 and 90 which extend through apertures in the side walls and are received by internal threads provided at the respective extremities of the guide bar 86. A bearing assembly 92 is connected for pivotal movement to the pivot arm 48 and is received for linear movement by the guide bar 86. As the bearing moves linearly along the guide bar, it will be pivotally rotatable about its pivotal point of attachment with the pivot arm 48. Thus providing for pivotal movement of the pivot arm 48 in the manner shown in full lines and broken lines in FIG. 3. The X-ray source 36 is supported at or near the rear portion of the pivot arm 48 and an X-ray film cassette holder 94 is fixed to the forward extremity of the pivot arm. The cassette holder 94 is adapted to receive an X-ray film cassette in adjustable relation therewith. The film cassette is maintained stationary during each X-ray exposure so that the X-ray image formed thereon is representative of a tomographic exposure made at the focal point 50.

For imparting controlled pivotal movement to the pivot arm 48 and the bearing 92 which is pivotally fixed thereto, the apparatus is provided with a motor support bracket 96 internally thereof which provides support for a reversible electric motor 98. A drive sheave 100 is fixed to the rotatable drive shaft of the motor 98 and receives a flexible drive element such as a drive cable 102. The drive cable is connected via a tension spring 104 with the linearly movable bearing 92. The opposite end of the flexible drive cable 102 is extended about an idler sheave 106 with its end fixed to the bearing structure 92. The idler sheave 106 is supported by an idler bracket 108 which is fixed internally of the side wall 22 as shown in FIG. 1. As the motor 98 is energized for driving in either direction, it imparts driving movement to the flexible drive element 102 which in turn imparts controlling linear movement to the bearing 92 and to the pivot arm 48 to which the bearing is pivotally connected. Thus as the electric motor is energized, the pivot arm 48 is pivotally moved, thereby causing pivotal movement between the full and broken line positions shown in FIG. 2.

For pivotal control of the motor 98, motor circuitry, typically provided within a protective enclosure such as shown at 110, includes limit switches 112 and 114 which are secured in spaced relation along the length of the guide bar 86. Thus as the pivot arm 48 reaches one extremity of its travel, it comes into contact with the control element of the limit switch 112 or 114, thereby deenergizing or reversing energization of the drive motor 98. As the pivot arm swings in one direction about the vertical axis 50, the X-ray source 36 is energized, thereby exposing film in a film cassette supported by the cassette holder 94. During its opposite pivotal travel, the X-ray source 36 will be deenergize. A tomographic cycle therefore occurs as the pivot arm 48 is moving in one pivotal direction. An operational cycle, however, occurs as the pivot arm 48 is pivotally moved through its tomographic imaging cycle and then returned by pivotal movement to its original starting point. The starting and ending point of its cycle is determined by positioning of the limit switches 112 and 114 relative to the guide bar 86. Electrical circuitry is also provided within a protective enclosure 116 located within the housing 12 for controlling energization of the X-ray source 36 such that tomographic exposure of the X-ray film occurs only during pivotal movement of the arm 48 in one direction.

The patient locator element 76 typically has the appearance of a mouthguard. It is a disposable element which is formed by having the patient bite on a body of uncured polymer material which, responsive to the force of biting, takes on the precise configuration of the patient's dentition. Thus, during the tomographic procedure, when the patient bites on the locator device 76 the patient's dentition will enter the depressions that occurred during formation of the locator device. The patient's dentition, and thus the respective alevolar arches of the patient will be precisely positioned with respect to the locator device. The apparatus of FIGS. 4 and 5 is thus positioned with the location pointer 56 in place within the vertical passage 54 as shown in FIG. 4 thus identifying the precise location of the focal point of the X-ray source. With the set screws 71, 72, 75 and 77 loose, the adjustment support 70 is positioned both vertically and rotatably about the locator rod 68 until the locator device 76 is located with its preselected area of interest precisely at the focal point defined by the lower pointed extremity 58 of the pointer element 56. After the locator device 76 has been properly located with respect to the focal point of the X-ray source, the pointer element 56 is removed from the vertical passage 54 thus enabling the patient to bite on the locator device 76. With the patient thus stabilized, the electrical circuitry of the motor 98 and the X-ray source 36 are controllably energized so as to execute a tomographic X-ray cycle wherein the pivot arm 48 is pivoted in one direction while the X-ray source is energized and then pivoted in the opposite direction for return to its starting point with the X-ray source deenergized. The anatomical site of interest can be very accurately positioned in this manner so that the tomographic X-ray image of the site will be very clear.

In view of the foregoing, it is evident that the present invention is one well adapted to attain all of the objects and features hereinabove set forth, together with other objects and features which are inherent in the apparatus disclosed herein.

As will be readily apparent to those skilled in the art, the present invention may be produced in other specific forms without departing from its spirit or essential characteristics. The present embodiment, is therefore, to be considered as illustrative and not restrictive, the scope of the invention being indicated by the claims rather than the foregoing description, and all changes which come within the meaning and range of the equivalence of the claims are therefore intended to be embraced therein.

What is claimed is:

1. Apparatus for cranial X-ray tomography and radiography comprising:

(a) a support arm being oriented substantially horizontally and having a pivot bearing having an axis of rotation, said pivot bearing having a passage being coincident with said axis of rotation;
   (b) an elongate guide bar for establishing a linear guide path;
   (c) an elongate pivot arm having a pivot axis, said pivot axis being coincident with said axis of rotation;
   (d) an X-ray source being fixed to said pivot arm on one side of said axis of rotation and being operative, when energized, for projecting a beam of X-radiation in intersecting relation with said axis of rotation and having a focal point at said axis of rotation;
   (e) an X-ray film cassette holder being fixed to said pivot arm and positioned to support an X-ray film cassette with the film thereof positioned to be exposed by said beam of X-radiation to form a tomographic X-ray image representing human anatomy located at said focal point;
   (f) a guide element being connected to said pivot arm and being linearly movable in guided relation along said linear guide path;
   (g) means for moving said pivot arm, said X-ray source and said X-ray film holder in arcuate manner about said axis of rotation with said X-ray source being energized for generation of said beam of X-radiation during predetermined pivotal movement in one rotational direction; and
   (h) means for fixing an anatomical site of interest of a patient at said focal point of said beam of X-radiation; and
   (i) a location pointer having upper and lower ends and being removably received within said passage and defining a location point at said lower end, said location pointer being of such length that when positioned within said passage said location point coincides with the intersecting point of said beam of X-radiation with said axis of rotation.

2. The apparatus of claim 1 wherein:
said pivot bearing establishing pivotal rotation of said pivot arm relative to said horizontal support at said axis of rotation and forming a passage therethrough being coincident with said axis of rotation.

3. The apparatus of claim 2, including:
an elongate location pointer being removably positionable within said passage and defining a locator point at one end thereof, said elongate location pointer being of such length for precisely locating said locator point at the point at which said axis of rotation in intersected by said beam of X-radiation.

4. The apparatus of claim 1, including:
   (a) a housing structure;
   (b) said elongate guide bar being horizontally disposed within said housing structure;
   (c) a guide bearing being disposed in linearly movable, guided relation with said elongated guide bar and being connected with said pivot arm; and
   (d) means for controllably moving said guide bearing along said elongate guide bar for imparting pivotal movement to said pivot arm about said axis of rotation.

5. The apparatus of claim 4 wherein said means for controllably moving said guide bearing relative to said elongate guide bar comprises:
   (a) a reversible electric motor having a drive shaft being fixed within said housing;

(b) a drive sheave being connected to said drive shaft and being rotatable thereby;
(c) a driven sheave being rotably supported within said housing; and
(d) an elongate drive element being received about said drive sheave and said driven sheave and having driving interconnection with said bearing.

6. The apparatus of claim 5, including:
(a) an electrical circuit for selective control of said reversible electric motor; and
(b) a pair of mechanically energized limit switches being coupled within said electrical control circuitry and being positioned for actuation responsive to predetermined pivoting of said pivot arm to thus define predetermine movement of said pivot arm during cranial X-ray tomography.

7. The apparatus of claim 1, including:
(a) a housing structure;
(b) said support arm being a horizontal support fixed to said housing structure;
(c) said pivot bearing being fixed to said horizontal support and defining said axis of rotation; and
(d) said elongate pivot arm being movably connected to said horizontal support by said pivot bearing.

8. The apparatus of claim 7, wherein:
said pivot bearing establishing pivotal connection of said elongate pivot arm to said horizontal support.

9. The apparatus of claim 1, wherein said location pointer further comprises:
(a) an elongate pointer shaft of predetermined length having said location point at said lower end; and
(b) an enlargement being provided at said upper end of said elongate pointer shaft and forming a stop shoulder for positioning engagement with said pivot bearing.

10. The apparatus of claim 1, including:
(a) a patient locator arm being fixed to said pivot arm; and
(b) a patient dentition locator being supported by said patient locator arm being adjustable relative to said patient locator arm for positioning a predetermined part of said patient dentition locator at said focal point of said X-ray source and in registry with said axis of rotation.

11. The apparatus of claim 10 wherein:
(a) said patient locator arm being fixed to said pivot bearing and projecting laterally therefrom;
(b) a locator rod projecting downwardly from said patient locator arm and being disposed in spaced, parallel relation with said axis of rotation; and
(c) a locator bracket being adjustably connected to said locator rod and having said patient dentition locator supported thereby.

12. Apparatus for cranial X-ray tomography and radiography comprising:
(a) a housing structure;
(b) a horizontal support being fixed to said housing structure and projecting forwardly therefrom, said horizontal support including an axis of rotation located forwardly of said housing structure;
(c) an elongate guide element being horizontally disposed within said housing structure;
(d) a pivot arm pivotally supported by said horizontal support at about said axis of rotation;
(e) an X-ray source being fixed to said pivot arm on one side of said axis of rotation and being operative, when energized, for projecting a beam of X-radiation in intersecting relation with said axis of rotation and having a focal point at said axis of rotation;
(f) an X-ray film cassette holder being fixed to said pivot arm and positioned to support an X-ray film cassette with the film thereof positioned to be exposed by said beam of X-radiation to form a tomographic X-ray image representing human anatomy located at said focal point;
(g) a linear bearing being received in linearly movable, guided relation with said elongate guide element and being pivotally connected to said pivot arm;
(h) a reversible electric motor being interconnected in driving relation with said linear bearing for moving said pivot arm, said X-ray source and and X-ray film holder in articulate manner about said axis of rotation with said X-ray source being energized for generation of said beam of X-radiation during predetermined pivotal movement in one rotational direction; and
(i) means for locating an anatomical site of interest of a patient at said focal point of said beam of X-radiation.

13. The apparatus of claim 12 including:
(a) a bearing element being provided on said horizontal support, said bearing element forming said axis of rotation; and
(b) said bearing establishing pivotal rotation of said pivot arm relative to said horizontal support at said axis of rotation.

14. The apparatus of claim 13, wherein:
(a) said bearing includes a vertical passage coincident with said axis of rotation; and
(b) an elongate location pointer is removably positionable within said vertical passage and defines a locator point precisely locating the point at which said axis of rotation is intersected by said beam of X-radiation.

15. The apparatus of claim 12 wherein said elongate guide element comprises:
(a) an elongate cylindrical guide bar being horizontally disposed within said housing; and
(b) said linear bearing being pivotally connected with said pivot arm.

16. The apparatus of claim 15, including:
(a) an electrical circuit for selective control of said reversible electric motor; and
(b) a pair of mechanically energized limit switches being coupled within said electrical control circuitry and being positioned for actuation responsive to predetermined pivoting of said pivot arm to thus define predetermined movement of said pivot arm during cranial X-ray tomography.

17. The apparatus of claim 12, including:
a pivot bearing establishing pivotal connection of said pivot arm to said horizontal support.

18. The apparatus of claim 17, wherein:
(a) said pivot bearing includes said axis of rotation;
(b) said pivot bearing including a passage being coincident with said axis of rotation, said passage and said axis of rotation being vertically oriented; and
(c) a location pointer being removably received within said passage and having upper and lower ends and a location point at said lower end, said location pointer being of such length that when positioned in said passage, said location point coincides with the intersecting point of said beam of X-radiation with said axis of rotation.

19. The apparatus of claim 18, wherein said location pointer comprises:
   (a) an elongate pointer shaft of predetermined length having a sharp point at the lower extremity thereof; and
   (b) an enlargement at the upper end of said elongate pointer shaft forming a stop shoulder for positioning engagement with said pivot bearing.

20. Apparatus for cranial X-ray tomography and radiography comprising:
   (a) a support arm having a pivot bearing forming an axis of rotation, said pivot bearing having a passage being coincident with said axis of rotation;
   (b) an elongate guide bar for establishing a linear guide path;
   (c) a pivot arm having apivot axis being coincident with said axis of rotation;
   (d) a linear bearing having linearly movable guided relation with said elongate guide bar and being connected to said pivot arm;
   (e) an X-ray source being fixed to said pivot arm on one side of said axis of rotation and being operative, when energized, for projecting a beam of X-radiation in intersecting relation with said axis of rotation and having a focal point at said axis of rotation;
   (f) an X-ray film cassette holder being fixed to said pivot arm and positioned to support an X-ray film cassette with a film thereof positioned to be exposed by said beam of X-radiation to form a tomographic X-ray image representing human anatomy located at said focal point;
   (e) said linear bearing being removably mounted along said elongate guide bar and thus moving said pivot arm about said pivot axis and thereby moving said X-ray source and said X-ray film holder in arcuate manner about said axis of rotation with said X-ray source being energized for generation of said beam of X-radiation during predetermined pivotal movement in one rotational direction; and
   (h) means for locating an anatomical site of interest of a patient at said focal point of said beam of X-radiation.

* * * * *